(12) United States Patent
Naumann

(10) Patent No.: US 8,354,079 B2
(45) Date of Patent: Jan. 15, 2013

(54) PIPETTING DEVICE

(75) Inventor: Uwe Naumann, Jena (DE)

(73) Assignee: CyBio AG, Jena (DE)

( * ) Notice: Subject to any disclaimer, the term of this patent is extended or adjusted under 35 U.S.C. 154(b) by 0 days.

(21) Appl. No.: 13/424,070

(22) Filed: Mar. 19, 2012

(65) Prior Publication Data

US 2012/0258026 A1      Oct. 11, 2012

(30) Foreign Application Priority Data

Apr. 8, 2011   (DE) .................... 20 2011 000 837 U

(51) Int. Cl.
*B01L 3/02*   (2006.01)

(52) U.S. Cl. ........ 422/511; 422/508; 422/509; 422/524; 422/525; 422/526; 422/63; 422/64; 422/65; 422/67; 422/68.1; 422/500; 73/863.32; 73/864; 73/864.01; 73/864.11; 73/864.14; 73/864.3

(58) Field of Classification Search .................. 422/500, 422/508–509, 511, 524–526, 564, 63–68.1; 73/863.32, 864, 864.01, 864.11, 864.14, 73/864.31

See application file for complete search history.

(56) References Cited

U.S. PATENT DOCUMENTS

| | | | |
|---|---|---|---|
| 4,554,839 A | | 11/1985 | Hewett et al. |
| 5,827,745 A | * | 10/1998 | Astle ................................ 436/54 |
| 6,426,047 B1 | * | 7/2002 | Hamel et al. ................... 422/526 |
| 6,582,664 B2 | * | 6/2003 | Bevirt et al. .................... 422/501 |
| 7,189,369 B2 | * | 3/2007 | Higuchi ........................ 422/511 |
| 7,585,463 B2 | * | 9/2009 | Austin et al. ..................... 422/63 |
| 7,897,111 B2 | * | 3/2011 | Naumann ...................... 422/511 |
| 2002/0176803 A1 | * | 11/2002 | Hamel et al. ................... 422/100 |
| 2003/0124735 A1 | * | 7/2003 | Nanthakumar et al. ....... 436/180 |
| 2003/0190264 A1 | * | 10/2003 | Yiu .............................. 422/100 |
| 2011/0009608 A1 | | 1/2011 | Kim et al. |

FOREIGN PATENT DOCUMENTS

| | | |
|---|---|---|
| DE | 92 04 388 U1 | 6/1992 |
| DE | 197 42 493 C1 | 2/1999 |
| DE | 100 48 637 A1 | 2/2002 |
| DE | 20 2005 006 970 U1 | 7/2005 |
| DE | 20 2008 013 533 U1 | 12/2008 |
| WO | WO 02/16 036 A2 | 2/2002 |
| WO | WO 02/096 562 A1 | 12/2002 |

* cited by examiner

*Primary Examiner* — Brian R Gordon

(74) *Attorney, Agent, or Firm* — Duane Morris LLP

(57) ABSTRACT

The invention relates to a sealing assembly for a metering device, in particular a multi-channel metering device. The sealing assembly serves to seal pipette tips with respect to the metering device. A multi-channel metering device comprises a multiplicity of openings arranged in one plane. A sealing plate with holes in the grid of the openings abuts this plane. Each pipette tip is provided with an annular collar which has an abutting face and is pressed against the sealing plate by force closure so as to enclose one hole.

8 Claims, 18 Drawing Sheets

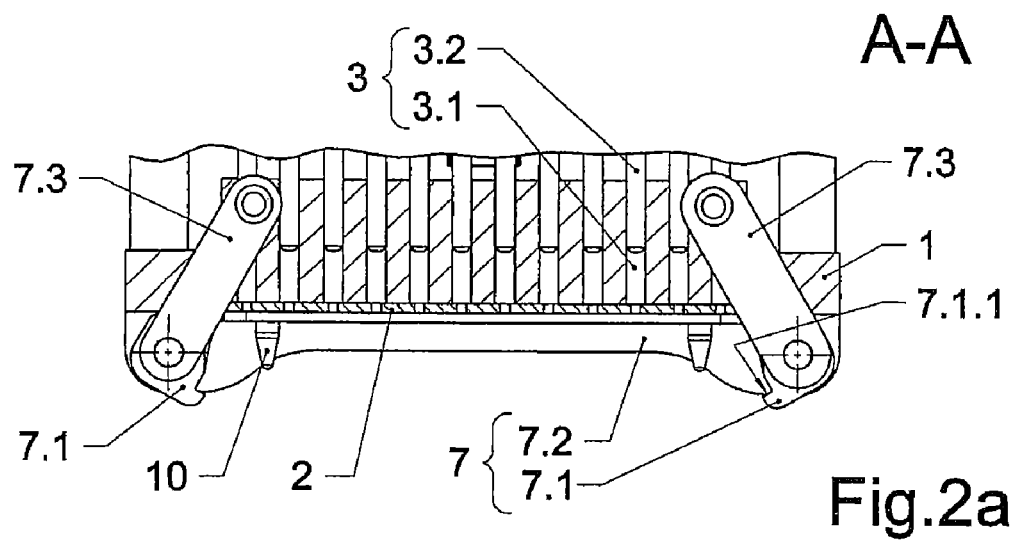
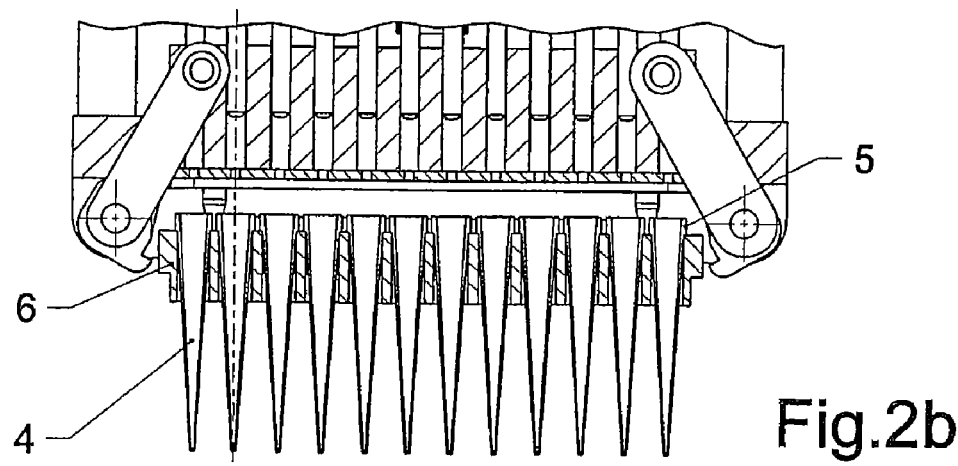

PIPETTING DEVICE

RELATED APPLICATIONS

The present application claims priority benefit of German Application No. DE 20 2011 000 837.1 filed on Apr. 8, 2011, the contents of each are incorporated by reference in their entirety.

FIELD OF THE INVENTION

The invention relates to a pipetting device that has a plurality of pipetting channels, which are arranged in a grid in a base plate and which in each case are formed in essence by a cylinder (sleeve) and a piston. The piston is guided in the cylinder and can be driven in a controllable manner. The device includes a magazine, which is populated with pipette tips, and which can be received in a magazine holder and can be lifted, in order to connect the pipette tips with the pipetting channels. Such a pipetting device is known, as described in the preamble, from DE 20 2008 013 533 U1.

BACKGROUND OF THE INVENTION

In order to accelerate the changing of the pipette tips, the magazine is not permanently connected to the pipetting device, but rather forms an integral unit with the pipette tips. This integral unit is detachable from the pipette device and, therefore, can be changed together with all of the pipette tips.

The magazines are rectangular plates with holes arranged in a grid and have, independently of the number of holes and, thus, the number of pipette tips that the holes can accommodate over the length and width of the plates, identical device-specific outer dimensions.

An important factor for ensuring the precision of the volume of fluid to be aspirated or dispensed through the pipetting channels is, inter alia, the hermetic seal between the sleeves and the pipette tips, which at present is solved by two different engineering principles.

In the case of the cone principle, which has been widely accepted for the manually operated single channel pipette and duplicated, the upper end of the pipette tips sits on or in cones formed on the sleeves. These cones hold the pipette tips in a force-locking manner and seal relative to the sleeves. This principle is associated with a plethora of drawbacks predominantly because of the inaccuracy of the pipette tips induced by the injection molding technology. A few examples that can be mentioned here include the uncertain simultaneous sealing of all of the pipette tips and the enormous upward lifting forces.

In order to avoid these drawbacks, a sealing principle, in which the ends of the sleeves that face the pipette tips extend into an elastic sealing plate, has established itself in parallel to the cone principle. In this case the pipette tips, with each tip enclosing one end of a sleeve, are sealed off from the sleeves indirectly by means of the sealing plate. For this purpose the pipette tips have a tip shoulder, from which the tips are suspended in a magazine and which presses the tips against the sealing plate.

The elastic sealing plate can be eliminated, if special pipette tips, which are made of two different synthetic plastic materials, are used. In the case of the pipette tips the actual tip body for aspirating reagents is made, like conventional pipette tips made of a synthetic plastic material, of polypropylene. In contrast, the tip shoulder is made of a thermoplastic elastomer, so that the pipette tips can be sealed off directly from the sleeves.

Since it is irrelevant for the description of a pipetting device according to the invention whether the pipette tips are sealed off indirectly by means of a sealing plate or directly by means of an elastic tip shoulder, the description below is based on a conventional sealing method by means of a sealing plate for the sake of simplicity.

In order to ensure a reliable seal, the magazine, in which the pipette tips are suspended from their tip shoulder, has to have an adequately high flexural rigidity.

Since the flexural rigidity of the magazine is determined by the choice of material or rather the material's modulus of elasticity and the moment of inertia of an area, the dimensions, in particular the thickness of the magazine, determine the flexural rigidity of the magazine, which is a hole plate.

A pipetting device according to the invention is based on the aforementioned second sealing principle.

In all of the prior art pipetting devices of this type, a magazine, populated with pipette tips, is pushed, like a drawer, into a vertically moveable magazine holder, which represents a frame that is open on one side, as far as an end stop and then is pulled or pushed (drawer principle) against the sealing plate with a very powerful drive of the frame. The frame has lateral guide faces and an end stop, in order to put the magazine in a defined position inside the frame so that the pipette tips are assigned to the sleeves in such a way that they are in alignment.

The drawback with the drawer principle is that free space in front of the pipetting device is absolutely mandatory to ensure accessibility for pushing and pulling the magazine in and out.

In the event that the tips are to be changed automatically, an additional handling device for pushing and pulling the magazine in and out is necessary. Free access to the pipetting device is also absolutely mandatory for this device. If the tips are not changed by a lab robot with a relatively large working area, then it is also necessary to provide storage places for magazines with fresh pipette tips and for magazines with used pipette tips in the immediate vicinity of the pipetting devices. To date deck systems have not used the pipetting devices according to the aforementioned second sealing principle.

Deck systems are automatic pipetting systems, in which all of the sample carriers, the reagent reservoirs and aids, like pipette tips, which are necessary for processing a specific laboratory task, are disposed stationarily in a so-called deck position so that they are accessible to a pipetting device that can be moved in three axes in order to reach each deck position. Access for a pipetting device or a gripper is routinely from the top, for which reason such deck systems known from the prior art use only pipetting devices with pipette tips that are connected to the pipetting channels according to the cone principle.

A pipetting device according to the aforementioned second sealing type, which is also used for a pipetting device according to the invention, is known from the utility model specification DE 20 2008 013 533 U1.

The pipetting device includes as the essential components or rather modules a base plate comprising passage bores, a pump system with a plurality of pipetting channels, comprising a sleeve, which is fitted into the passage bores, an elastic sealing plate with holes and a magazine, populated with pipette tips. In this case the passage bores and consequently, fitted therein, the sleeves, the holes of the sealing plate and the pipette tips are arranged in an identical grid on a common mechanical axis. The magazine is connected by means of a gear mechanism to a drive motor.

The gear mechanism translates the rotary motion and the torque of the drive motor into a linear lifting motion and a tightening force acting on the magazine holder.

The result is that the pipette tips are lifted up to the sealing plate and, coaxially enclosing the sleeves, are pressed by means of their shoulder against the sealing plate with an adequately large tightening force, so that the pipette tips are sealed off from the sleeves.

The magazine and the magazine holder are designed according to the utility model specification DE 20 2008 013 533 U1 in such a way that the magazine can be inserted into the magazine holder like a drawer.

The major distinction between the other pipetting devices of this kind and the pipetting device according to the utility model specification DE 20 2008 013 533 U1 lies in the design of the tightening of the magazine. The rotary motion generated by a drive motor is translated by way of two identical eccentric gear mechanisms into a lifting motion of the magazine frame. In this case the eccentric gear mechanism is mounted on the base plate so as to be fixed relative to the frame. For this reason the housing of the pipetting device remains completely unaffected by the force transmission path when tightening the magazine.

The pipetting device, according to the utility model specification DE 20 2008 013 533 U1, has the same drawbacks as the above-described pipetting devices that were designed on the basis of the drawer principle.

SUMMARY OF THE INVENTION

The object of the present invention is to provide a new pipetting device with a lower space requirement for feeding magazines.

This engineering object is achieved by a pipetting device comprising a base plate; a plurality of pipetting channels, which are arranged in a defined grid in the base plate; a magazine, which is populated with the pipette tips in the same grid, each of these tips having a tip shoulder; a magazine holder; a drive motor and a gear mechanism, which connects together the magazine holder and the drive motor, so that the magazine can be moved vertically between an aspirating and dispensing position and a sealing position, in which the tip shoulders are non-positively connected to the pipetting channels in such a way that said tip shoulders and pipetting channels are sealed off from each other, characterized in that in the aspirating and dispensing position the magazine holder is in an open state, in which it forms a passage opening larger than the magazine, so that the magazine can be inserted into the magazine holder from the bottom; and that in the sealing position the magazine holder is in a closed state, in which the support surfaces, against which the magazine rests, project into the passage opening; and that the gear mechanism is designed in such a way that, when it is driven, not only is the magazine moved vertically, but also the magazine holder is moved into the said positions.

The magazine holder comprises in an advantageous manner a closed magazine frame having a free interior that forms the passage opening and has latches, which can be axially displaced in the horizontal direction and form the support surfaces in the closed state.

As an alternative, the magazine holder can comprise advantageously two swivel claws with free ends, which define the passage opening in the open state and form the support surfaces in the closed state.

It is provided advantageously that the magazine has centering cones and that the base plate has centering openings, in which the centering cones can be inserted.

The gear mechanism comprises in an advantageous manner a worm gear, which has an eccentric shaft, which is mounted on the output side and on which a tension coupling link is mounted in a rotatable manner about one of its ends; and its other end is connected to the magazine frame.

As an alternative, the gear mechanism comprises in an advantageous manner a worm gear; and attached to it on the output side is an eccentric shaft, on which a tension coupling link is mounted in a vertically displaceable manner, its ends are connected to claw arms, on which the swivel claws are formed and are so positively driven that the swivel claws execute a combined swivel and lifting motion.

An advantageous feature is that the base plate has stop plates with inclined sliding faces, against which an outer end of the latches rests so that the latches are displaced during the vertical motion.

The two swivel claws exhibit advantageously axes of rotation that are mounted in a rotatable manner in two bearing plates, which are connected to the base plate, and that are rigidly connected to one end of two lever arms, their other ends being connected to the gear mechanism, so that the swivel claws execute a swivel motion.

BRIEF DESCRIPTION OF THE DRAWINGS

The pipetting device is explained in detail below by means of exemplary embodiments with reference to the accompanying drawings.

Referring to the drawings:

FIGS. 2a-d are in each case a cross sectional view of a pipetting device according to FIG. 1 in four different states.

DESCRIPTION OF THE DRAWINGS

Figure 1A:
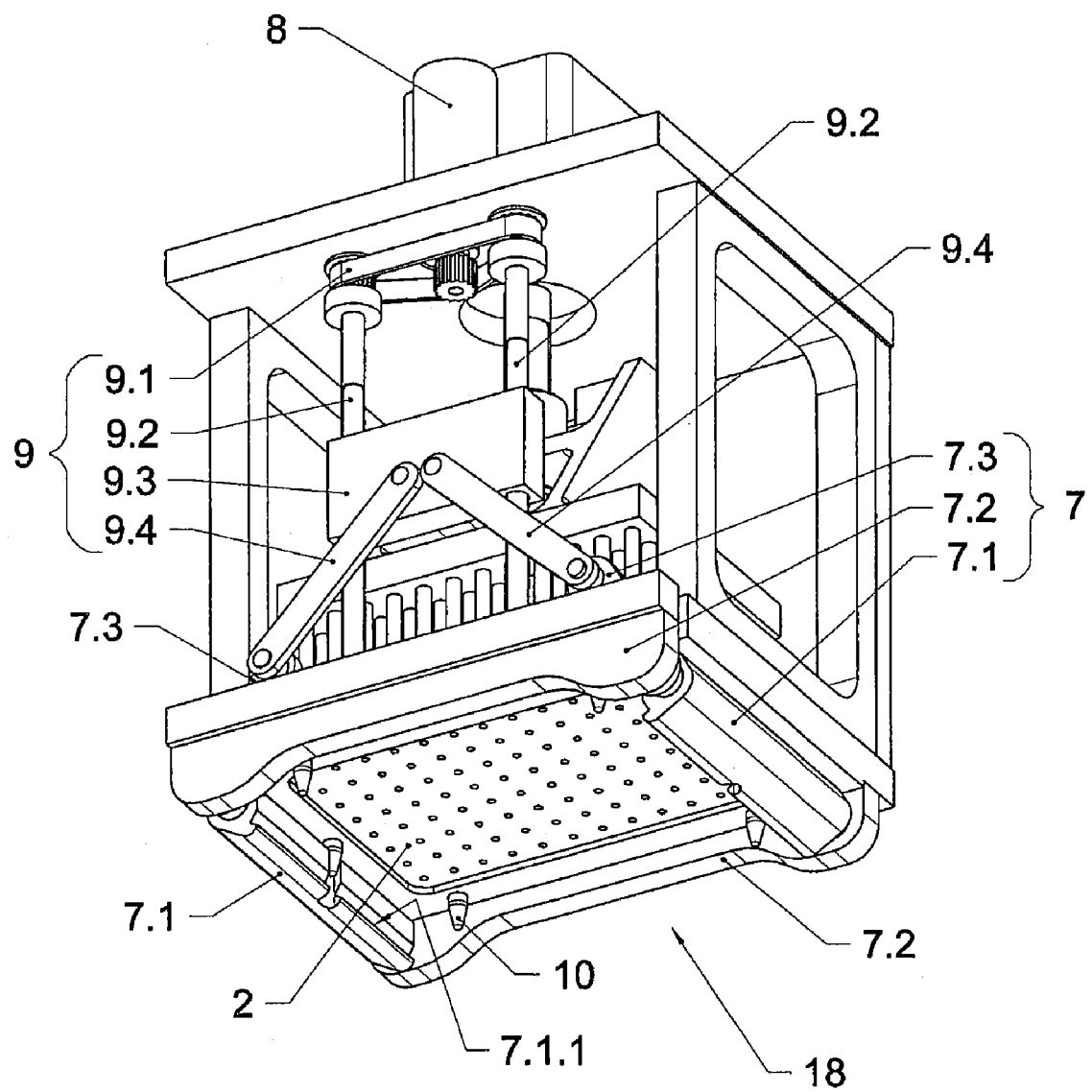
FIGS. 1a-b are in each case a perspective view of a pipetting device according to a first exemplary embodiment in the open and closed state.

FIGS. 1, 2 show a pipetting device according to a first exemplary embodiment. Before describing the details of this first embodiment, the common features that this first embodiment shares with the pipetting device known from the prior art shall be described in brief with reference to these figures.

Like the prior art pipetting device, the pipetting device according to the invention has in essence a base plate 1, a pump system with a plurality of pipetting channels 3, a sealing plate 2, a magazine holder 7 for receiving a magazine 6, populated with pipette tips 4, and a drive motor 8, which is connected to the magazine holder 7 by means of a gear mechanism 9, in order to connect the pipette tips 4 indirectly with the pipetting channels 3.

The sealing plate 2 can be omitted, if special pipette tips, which lend themselves well to sealing, are used as mentioned in the prior art. The rest of the design of the pipetting device is unaffected.

The base plate 1 is a totally flat, flexurally rigid plate. A housing frame 15 is connected along the periphery of the plate. On the housing frame is mounted in parallel to the base plate 1 a weight-bearing cover plate, on which a stepper motor for the pump system and a drive motor 8 are mounted.

In the base plate 1, a predefined grid has a plurality of passage holes 3.1, which form, as shown here in a very simplified form in FIG. 2, the cylinder of a pipetting channel 3, in which a piston 3.2 is guided. In reality, however, a sleeve is integrated into the respective passage holes 3.1. This sleeve also projects into the sealing plate 2; and there are seals, which also act as a guide, by means of which the pistons 3.2 are sealed off from the base plate 1. Since the exact design of the pipetting channels 3 is immaterial for the invention, and they would only make the figure unnecessarily more complicated, the pipetting channels 3 have been highly simplified, that is, depicted only by the piston 3.2 and the cylinder (passage hole 3.1).

Attached to the base plate 1 is the sealing plate 2, which rests flat against the side facing away from the housing frame 15. This sealing plate has passage holes 3.1 in a grid configuration that is identical to that of the base plate 1.

Located underneath the base plate 1 is the magazine holder 7, which can be moved relative to the base plate 1 and into which the magazine 6, populated with pipette tips 4, is inserted and can engage vertically with the sealing plate 2 and, thus, with the base plate 1.

The base plate 1 serves as a contact pressure plate, on the one hand, and, on the other hand, as a base for a frame-mounted arrangement of the drive motor 8 and a gear mechanism 9, which connects the drive motor 8 to the magazine holder 7.

The magazine 6 and the base plate 1 are totally flat and flexurally rigid plates so that the pipette tips 4 can be uniformly pressed with their tip shoulders 5 onto the sealing plate 2.

The above description of a pipetting device relates to both a pipetting device according to the prior art and also a pipetting device according to the invention.

The major distinction lies in the different design of the magazine holder 7 and consequently the magazine 6 and the gear mechanism 9.

The magazine holder 7 is designed in such an advantageous way that the distance between the support surfaces 7.1.1, 11.3.1, 13.1, against which the magazine 6 rests, is less, compared to the prior art, and is uniformly distributed at the edge of the magazine 6. This feature allows the use of magazines 6 that exhibit less flexural rigidity. The flexural rigidity, which has to be higher with the increasing number of accommodated pipette tips 4, is attained not only through the choice of a different material or other dimensions, but also, in particular, through more support surface 7.1.1, 11.3.1, 13.1, which can counteract the contact pressure force as the back support.

At this point four different exemplary embodiments, which differ essentially in the design of the magazine holder 7, 11, 13, are described below. In contrast to the prior art, they have in common that the magazine holder 7, 11, 13 can be moved from an open state, in which the magazine 6 can be lifted vertically into the magazine holder 7, 11, 13 (aspirating and dispensing position), into a closed state, in which the magazine 6 rests in a defined position in the magazine holder 7, 11, 13 (sealing position).

In the open state the magazine holder 7, 11, 13 forms a passage opening 18 that is larger than the magazine 6, so that the magazine 6 can be inserted into the magazine holder 7, 11, 13 from the bottom.

In the closed state the support surfaces 7.1.1, 11.3.1, 13.1.1, against which the magazine 6 rests, project into the passage opening 18.

According to the first exemplary embodiment, shown in FIGS. 1 and 2, the magazine holder 7 comprises two swivel claws 7.1, arranged opposite each other and having support surfaces 7.1.1; two bearing plates 7.2, which are provided with two rotary bearings for the swivel axes of the swivel claws 7.1; and two lever arms 7.3, which are rigidly connected to the swivel axes of the swivel claws 7.1.

Figure 2C:
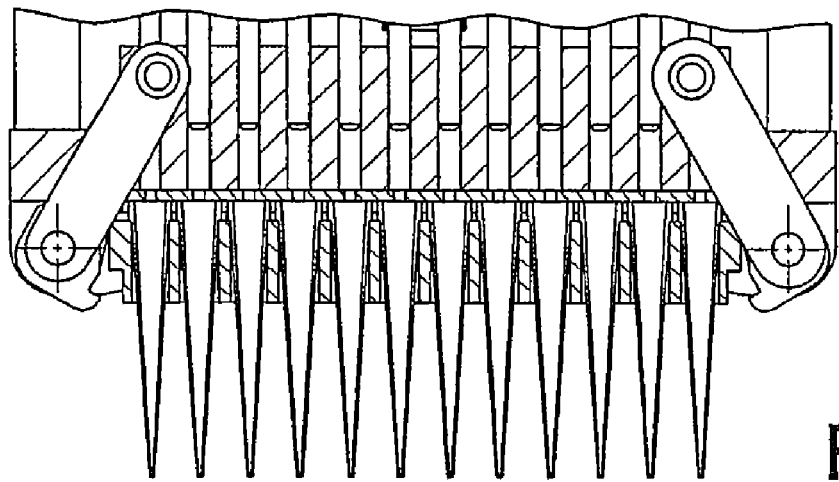
Figure 2D:
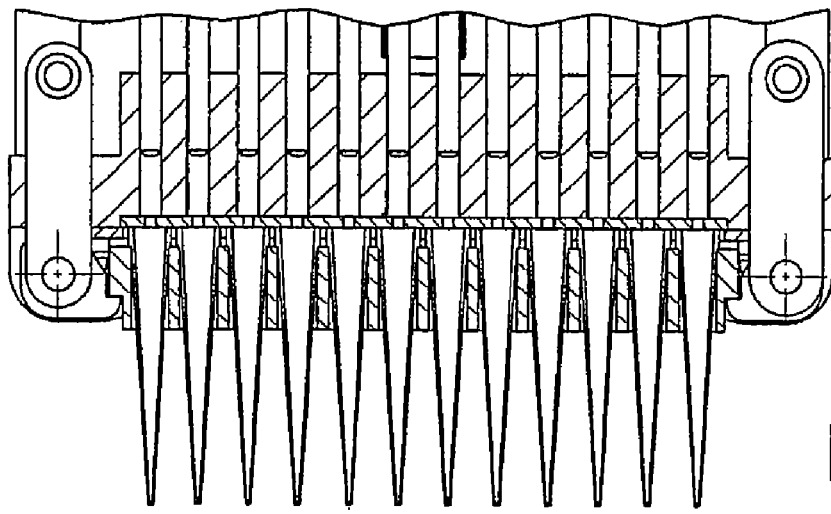

FIG. 1a shows the magazine holder 7 in an open state, in which the magazine 6 can be lifted between the swung-out swivel claws 7.1 and continues until it reaches the sealing plate 2.

Figure 1B:
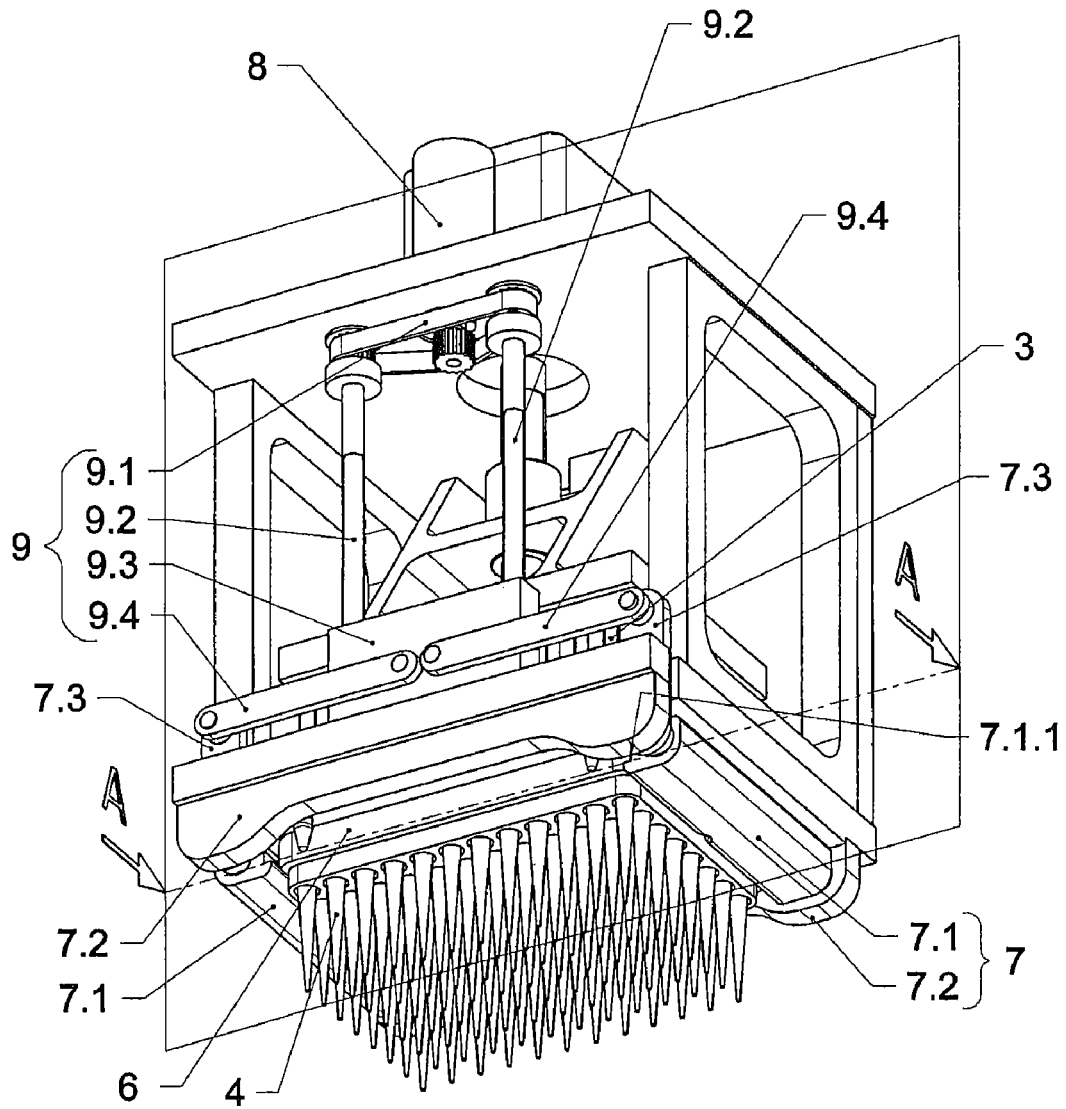

FIG. 1b shows the magazine holder 7 in a closed state, in which the magazine 6 rests on support surfaces 7.1.1 of the swung-in swivel claws 7.1.

FIGS. 2a-d are in each case a sectional view of not only the two states, depicted in FIG. 1, but also two intermediate states.

The drive motor 8 is connected to the lever arms 7.3 by means of a gear mechanism 9.

The output shaft of the drive motor 8 has an output pinion, which drives a toothed belt 9.1, which moves two threaded spindles 9.2 in synchronous rotary motion. A double drive nut 9.3 wanders up and down on the threaded spindles 9.2 according to the direction of motion.

Two sliding couplings 9.4 are mounted in a rotatable manner on two pins that are formed on the drive nut 9.3; and these sliding couplings transmit the motion to the lever arms 7.3.

In order for the magazine 6 to be received, the magazine holder 7 has to be in an open state (FIGS. 1, 2a-c).

In this open state the magazine 6, which is populated with pipette tips 4, is moved through the open swivel claws 7.1 and continues until it rests against the sealing plate 2.

Before the pipette tips 4 reach the sealing plate 2, the magazine 6 is put in the correct position relative to the pipetting channels 3 by means of centering cones 10, so that the axes of symmetry of the pipetting channels 3 and the pipette tips 4 line up (FIG. 2b).

In order to tighten the magazine 6 at the sealing plate 2 and to seal off the pipette tips 4 from the pipetting channels 3, the drive motor 8 sets the two threaded spindles 9.2 rotating in such a way that the drive nut 9.3 moves downward.

This action causes the two sliding couplings 9.4 to push the lever arms 7.3 outwards, so that the swivel claws 7.1 are rotated beneath the edge of the magazine 6 and make contact there. When said swivel claws are further rotated, the pipette tips 4 are pressed with their tip shoulders 5 against the sealing plate 2.

The sliding couplings 9.4 and the lever arms 7.3 form two toggle levers, so that at constant speed of the drive motor 8 the swivel claws 7.1 initially rotate very fast beneath the magazine 6 and then slowly lift the magazine 6.

The further the sliding couplings 9.4 move into their horizontal position, the slower, but more powerfully the swivel claws 7.1 rotate. In this way it is possible to generate large contact pressure forces with a small drive power of the drive motor 8 and yet quickly cover the first portion of the rotation.

The pipette tips 4 are detached from the sealing plate 2 in the reverse order of sequence.

When the swivel claws 7.1 are opened, it is also possible, in contrast to the above-described drawer principle, to toss the used and contaminated magazine 6 directly into a waste chute.

Figure 3A:
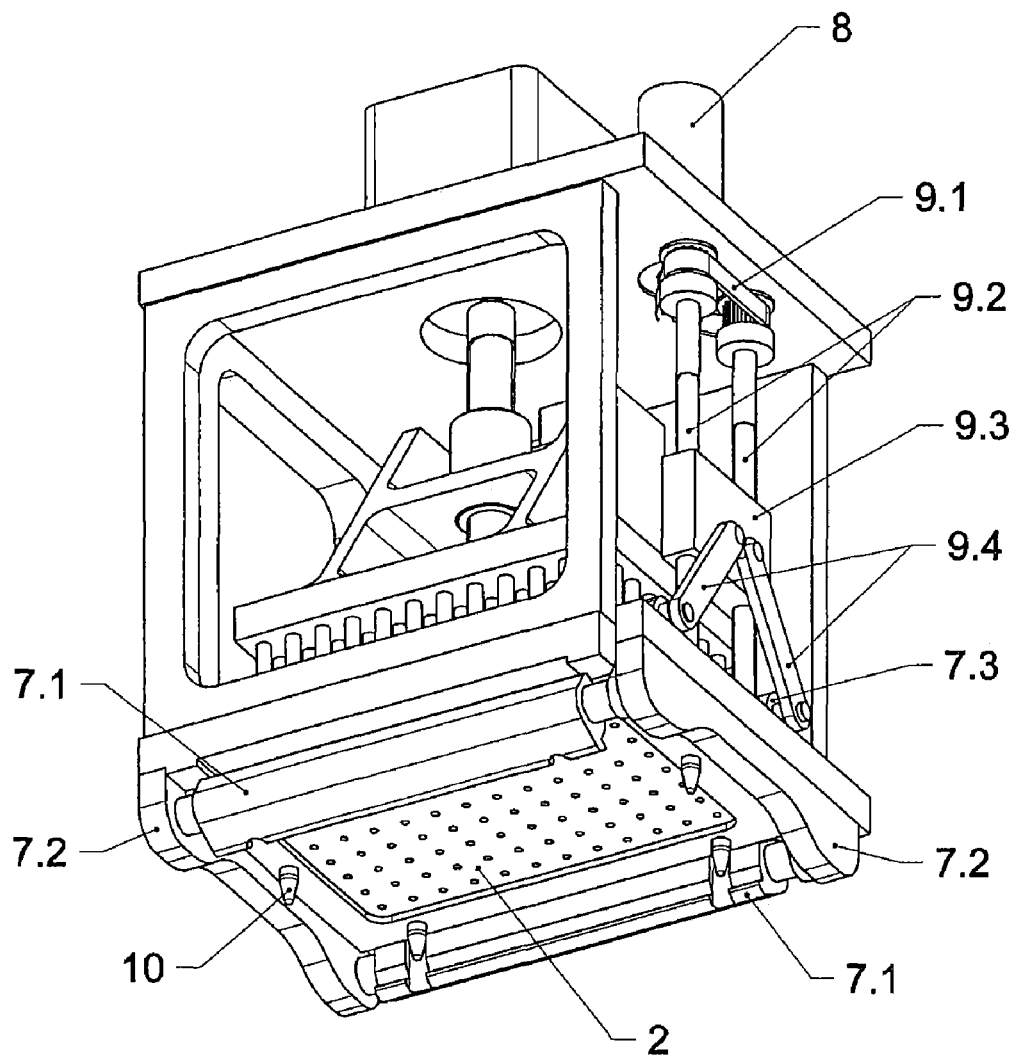
FIGS. 3a-b are in each case a perspective view of a pipetting device according to a second exemplary embodiment in the open and closed state.
Figure 3B:
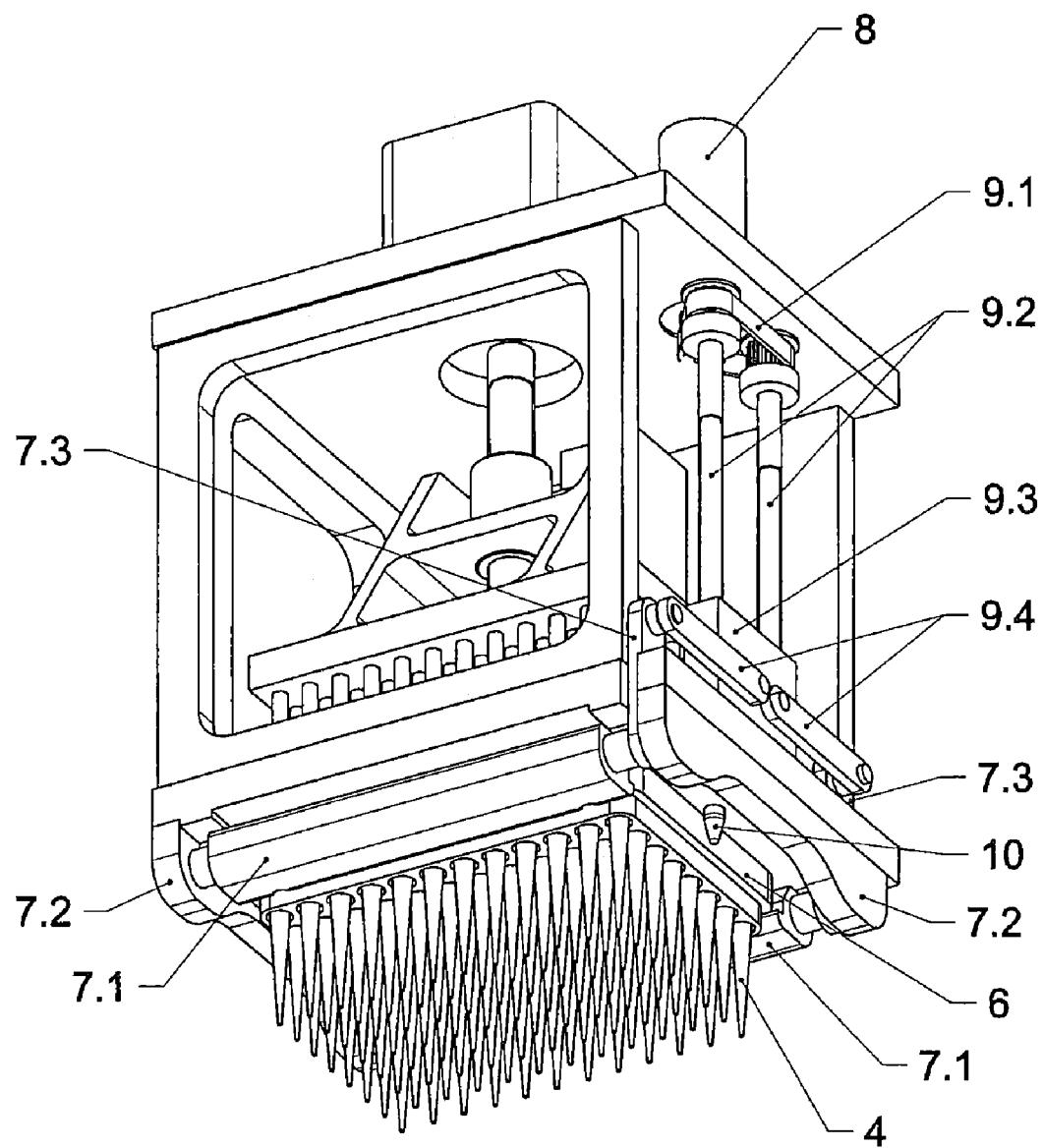
Figure 4A:
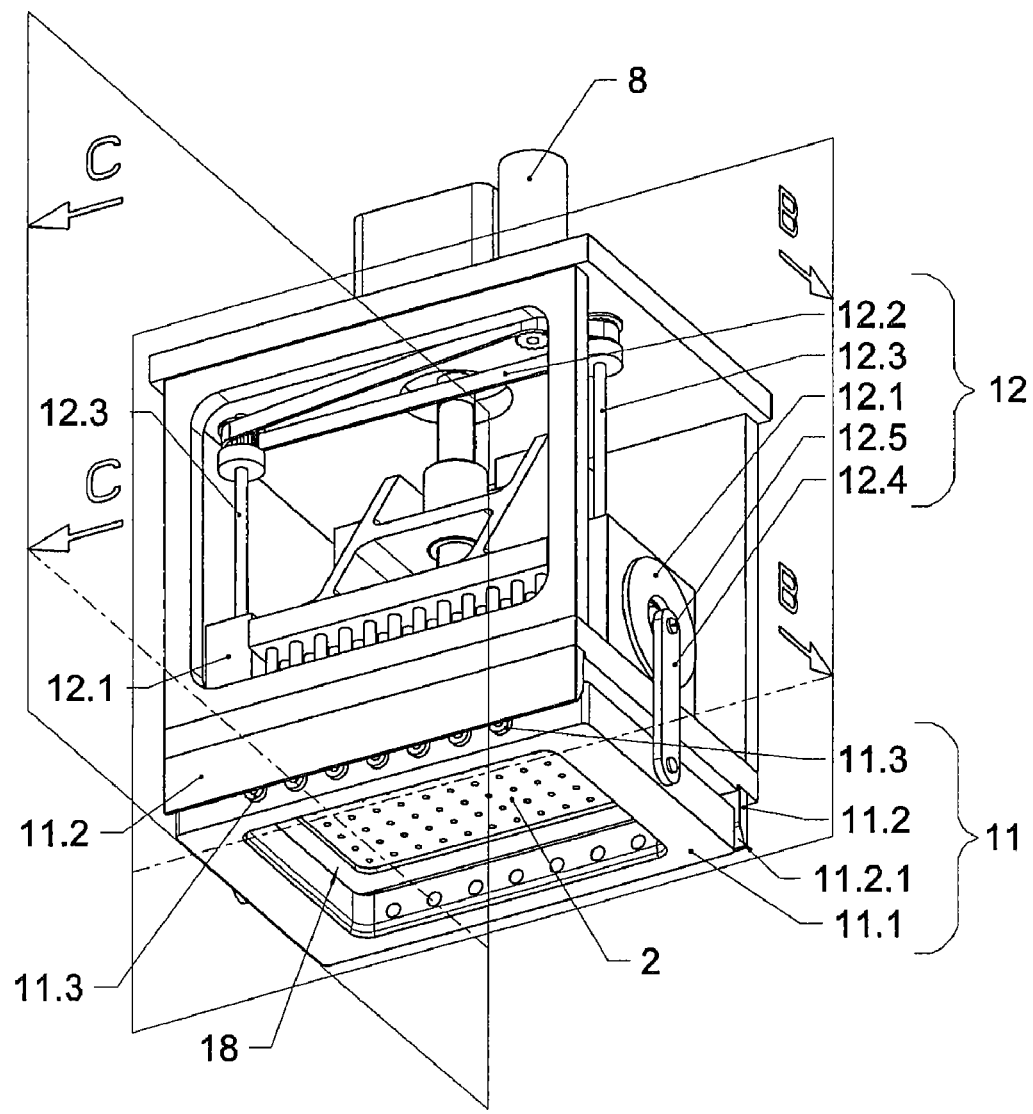
FIGS. 4a-b are in each case a perspective view of a pipetting device according to a third exemplary embodiment in the open and closed state.
Figure 4B:
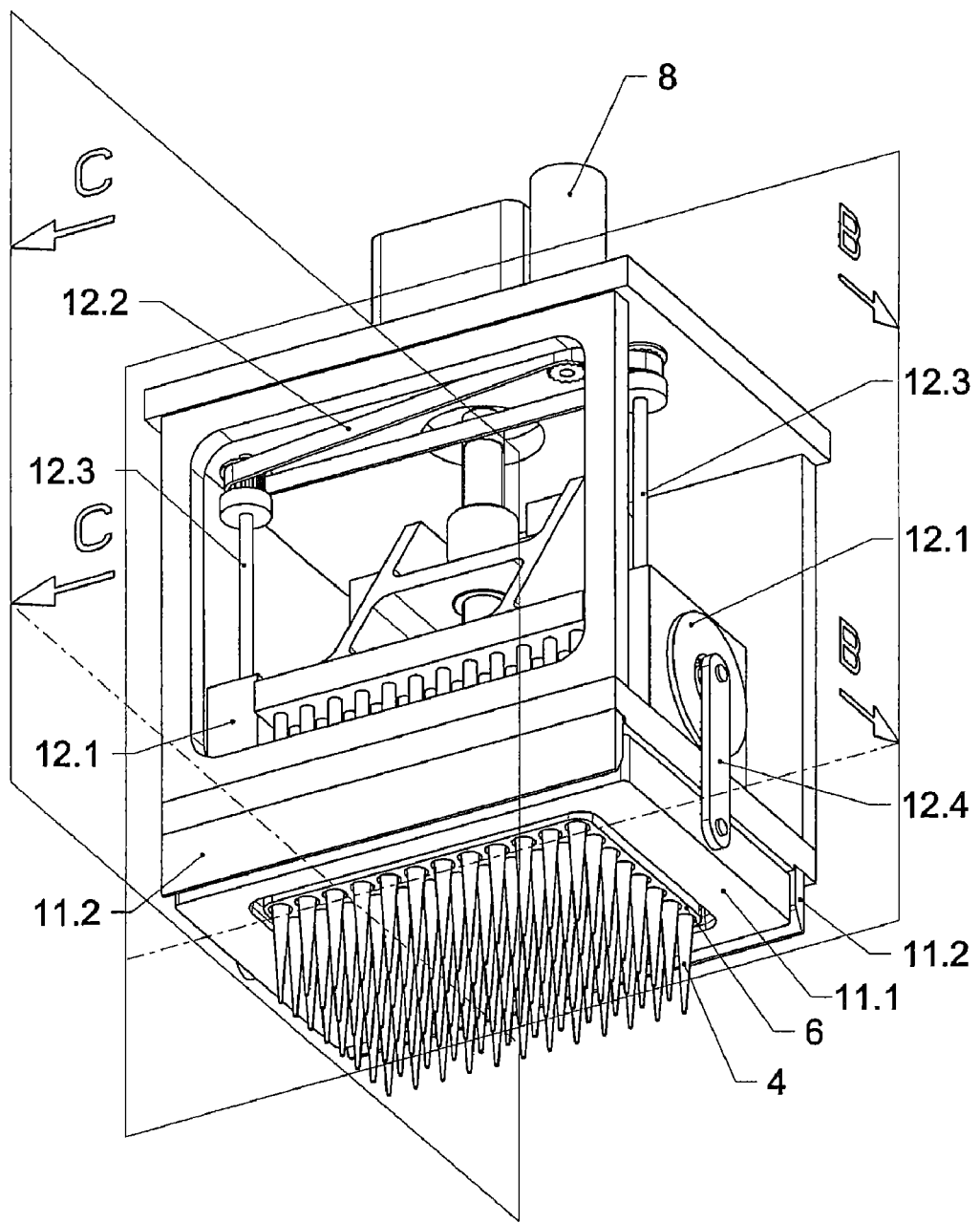
Figure 5:
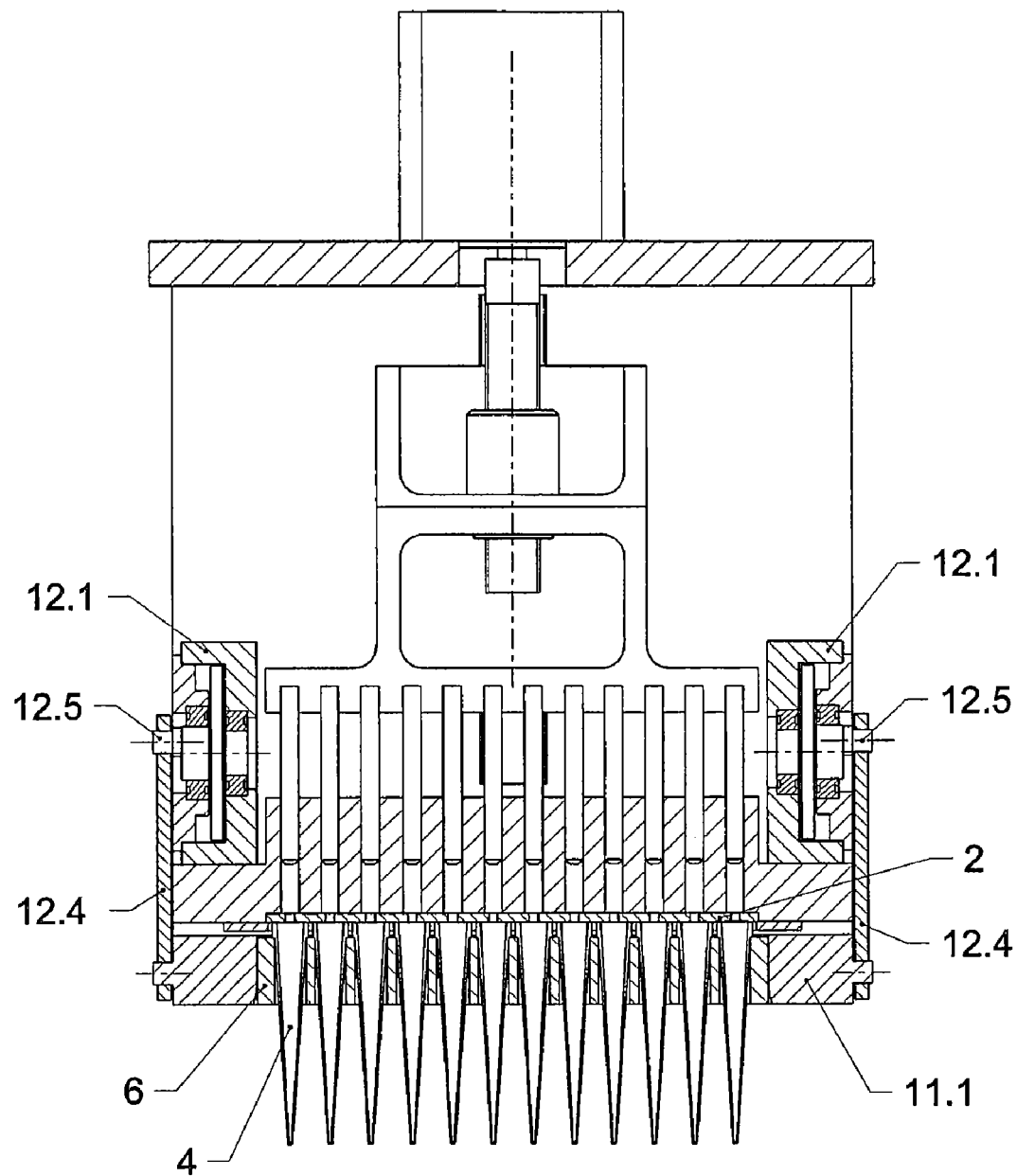
FIG. 5 is a first cross sectional view of a pipetting device according to FIG. 4b.

A second exemplary embodiment, shown in FIGS. 3a-b, differs from the first exemplary embodiment in that the pipetting device is configured in such a way that the swivel claws 7.1 do not reach under the shorter sides (broad sides) of the magazine 6, but rather reach under its longer sides (longitudinal sides).

The advantage of this second embodiment lies in the fact that the magazine 6 deflects over-proportionally less due to the bending length (8 to 12) which is shorter by ⅓. The pipette tips 4 are frequently changed chiefly for applications, where it is absolutely mandatory that there be no carryover whatsoever.

In order to accelerate this process, not only the contaminated pipette tips 4 are discarded after every use, but also the populated magazine 6.

For this reason the magazines 6 are made preferably of an inexpensive, filled synthetic plastic material. High strength plastics are ruled out for price reasons.

Despite any filling, such magazines 6 deflect more than metal magazines of the same thickness when the pipette tips 4 make contact and seal.

Since the mandatory contact pressure force rises with the number of pipette tips 4 to be sealed, it is unreliable to apply pressure on only the broad sides of the magazine 6, especially in the case of pipetting devices with more than 96 pipette tips 4.

If, on the other hand, pressure is applied on the two longitudinal sides, then the deflection can be controlled even without three-sided support.

A third exemplary embodiment 3, shown in FIGS. 4a-b, 5 and 6a-d, differs from the two aforementioned exemplary embodiments in the design of the magazine holder 11 and a gear mechanism 12.

In this case the magazine holder 11 is formed in essence by a magazine frame 11.1 that is closed on four sides and has latches 11.3, which can be moved transversely to the lift direction; and these latches have support surfaces 11.3.1. In order to displace the latches 11.3, there are two stop plates 11.2 with gliding surfaces 11.2.1, along which the latches 11.3 can be displaced in a gliding manner in their axial direction against a compression spring 11.4

In the open state of the magazine holder 11 the latches 11.3 are totally retracted into the passage holes 3.1 subject to the action of the compression springs 11.4 and do not project into the free interior of the magazine frame 11.1, which forms the passage opening 18. The dimensions of the free interior are slightly larger than the outside dimensions of the magazine 6, so that the magazine 6 can be lifted into the free interior and pass out of said interior or inversely can be lowered into the free interior and pass out of it.

In the closed state of the magazine holder 11 the latches 11.3 project into the free interior counter to the action of the compression springs 11.4, so that the latches 11.3 provide support surfaces 11.3.1 for the magazine 6 along two sides that lie opposite each other.

The gear mechanism 12 comprises in essence a toothed belt 12.2, two drive shafts 12.3, two worm gears 12.1, two eccentric shafts 12.5 and two tension coupling links 12.4.

The closed solid magazine frame 11.1 and the use of the worm gears 12.1 make this design very sturdy.

The drive motor 8 drives by means of the toothed belt 12.2 and the two drive shafts 12.3 the two self-locking worm gears 12.1, each of which is provided with an eccentric shaft 12.5 on the output side. The two tension coupling links 12.4 are mounted on the eccentric shafts 12.5. The rotary motion of the worm gears 12.1 is transformed by way of the tension coupling links 12.4 into a lifting motion of the magazine frame 11.1 that is connected to said tension coupling links by means of rotary bearings.

The free sides of the magazine frame 11.1 have cross bores, in which the latches 11.3 can glide.

Figure 6A:
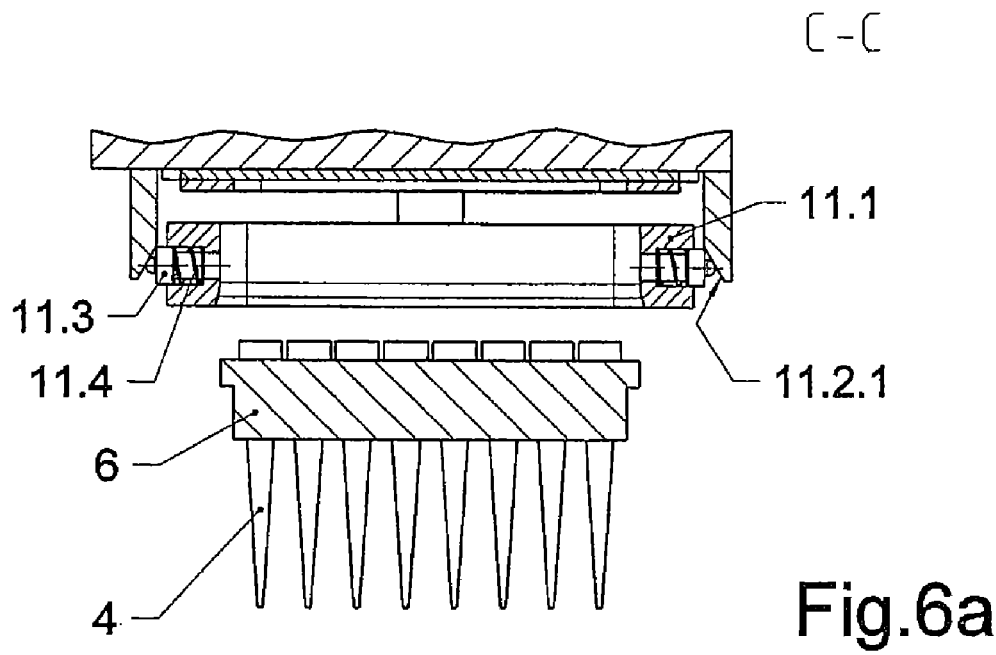
FIGS. 6a-d are in each case a second cross sectional view of a pipetting device according to FIGS. 4a-b in four different states.
Figure 6B:
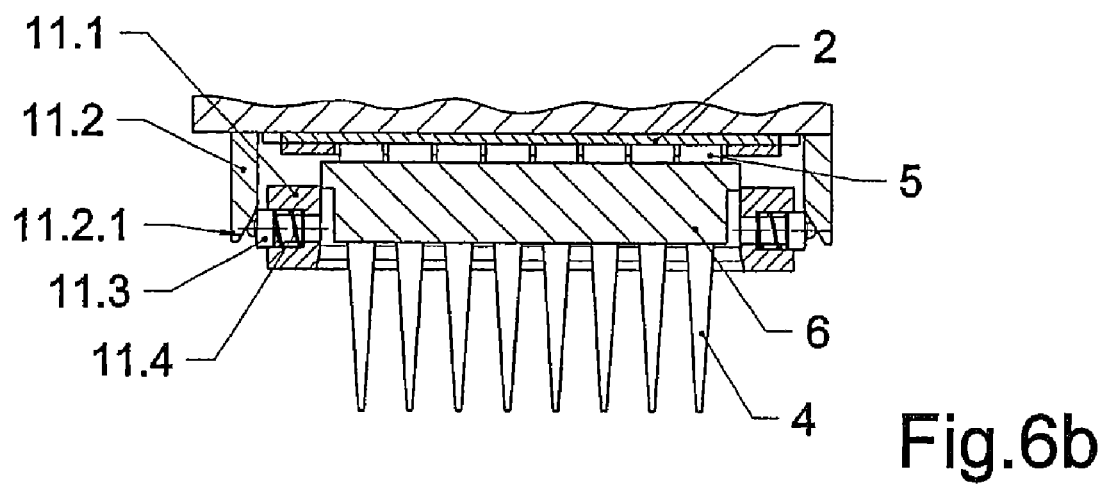
Figure 6C:
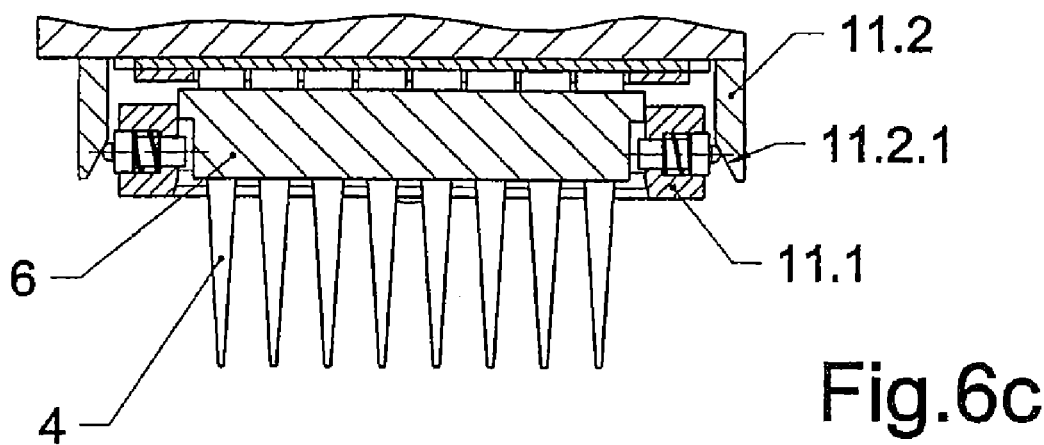
Figure 6D:
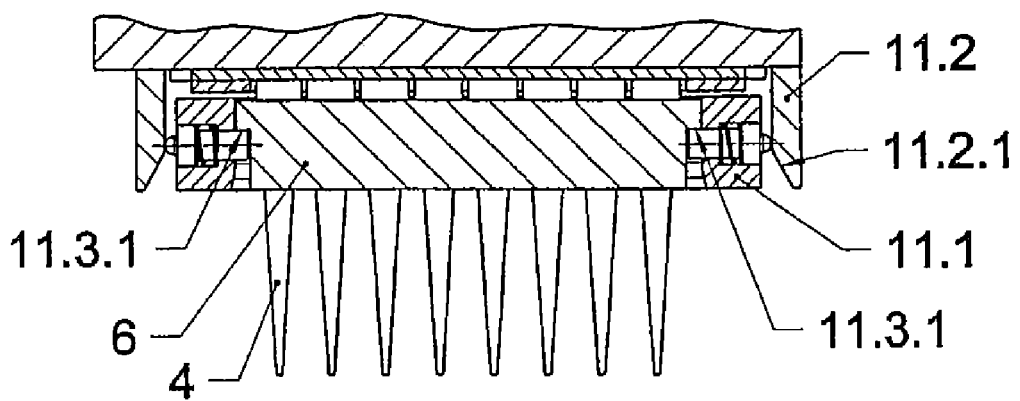
Figure 7A:
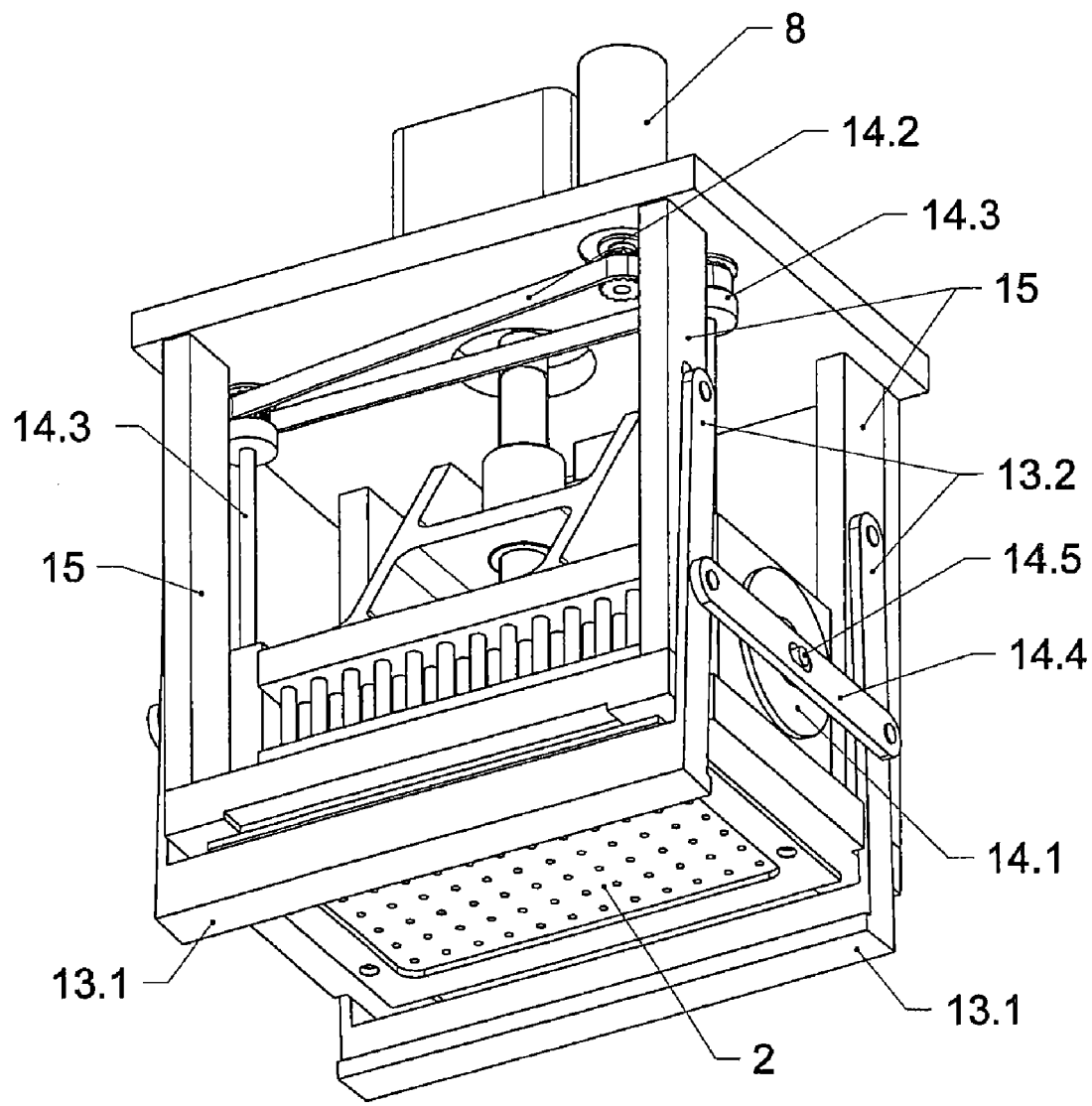
FIGS. 7a-b are in each case a perspective view of a pipetting device according to a fourth exemplary embodiment in the open and closed state.
Figure 7B:
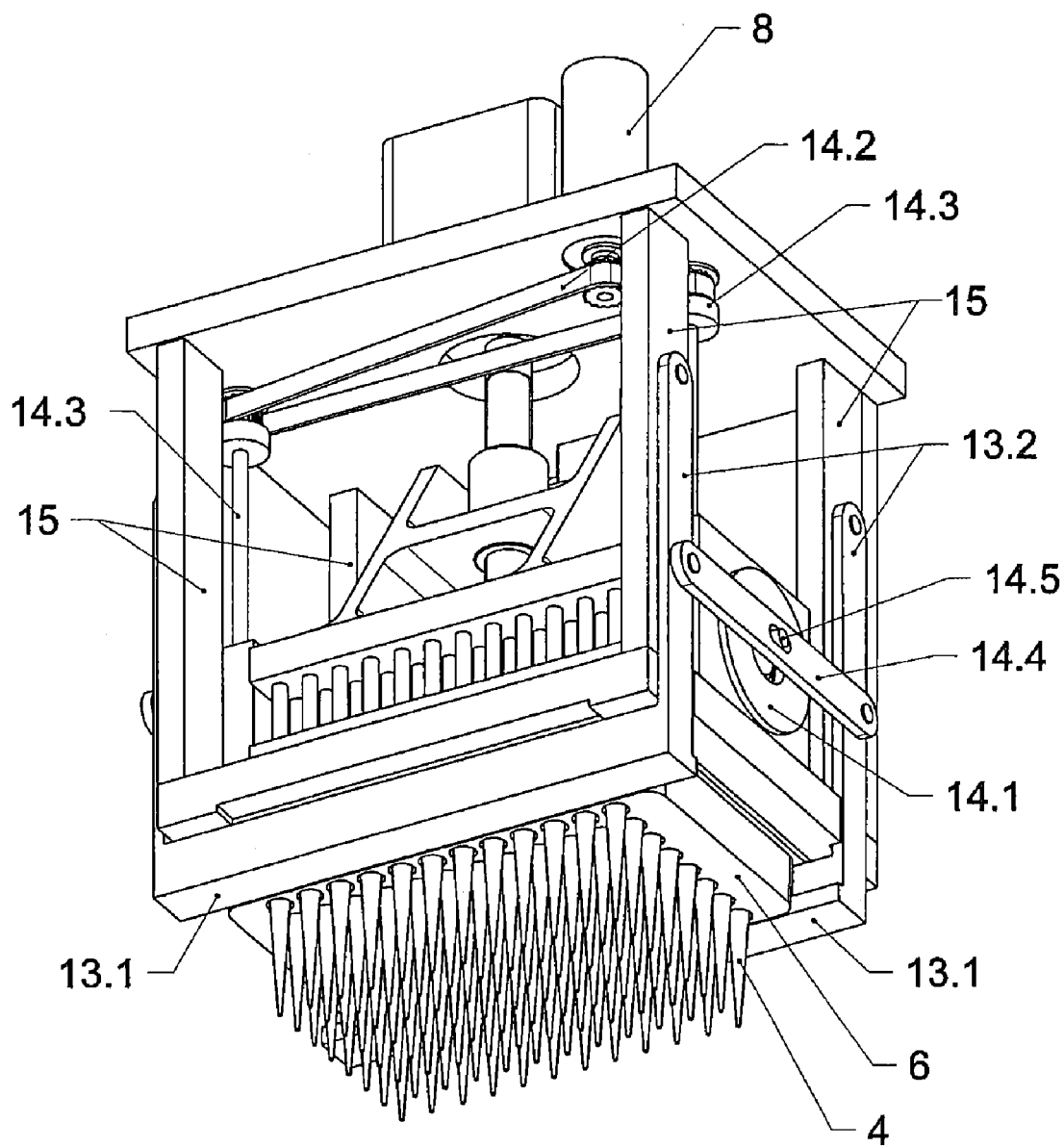

The operating principle of a pipetting device according to this third exemplary embodiment is shown in the FIGS. 6a-c.

To begin with, the magazine holder 11 is in the open state. That is, the magazine frame 11.1 is lowered; and the latches 11.3 do not project into the free interior of the magazine frame 11.1.

The latches 11.3 are pushed by the compression springs 11.4 out of the magazine frame 11.1 until they rest with their outer ends against the gliding surfaces 11.2.1 of the stop plates 11.2.

The magazine 6, populated with pipette tips 4, is beneath the pipetting device.

In principle, in order to carry out the pipetting process, the pipetting device and, thus, the pipette tips 4 and a holding container, such as a microtiter plate, from which the fluid is to be removed or into which the fluid is to be delivered, must be moveable relative to each other in the vertical direction. This movability allows the magazine 6 to be moved up to the sealing plate 2 until the tip shoulders 5 of the pipette tips 4 rest against the sealing plate 2 without exerting a force on said sealing plate.

Then the magazine frame 11.1 is pulled upwards. In the first segment of this path the latches 11.3 glide on the gliding surfaces 11.2.1, which slope relative to the axes of the latches 11.3, so that as the distance to the sealing plate 2 decreases, the latches 11.3 are pushed further and further into the free interior of the magazine 6.

In the last segment of the path, when the eccentric shafts 12.5 generate their highest force, the latches 11.3 are pushed completely under the magazine 6; and the pipette tips 4 are pressed against the sealing plate 2. A hermetic seal of the pipette tips 4 is reached; and the self-locking of the worm gears 12.1 maintains this state.

Since the latches 11.3 can be displaced with practically no force, an active drive of the latches 11.3 for displacement would also be easy to solve.

In this case the lifting path could be reduced to a few tenths of a millimeter, since gliding along a gliding surface 11.2.1 would be superfluous. Although such a design would need an additional small weak drive, the result would be a gain in the amount of time that is required for changing the pipette tips 4.

Such a design would be advantageous for applications, where the pipette tips 4 have to be frequently changed and the amount of time required for this change has a limiting effect.

The fourth exemplary embodiment is a combination of the above-described exemplary embodiments and is shown in the FIGS. 7a-b and 8a-d.

Comparable to the second exemplary embodiment, a magazine holder 13 comprises swivel claws 13.1, which reach under the longitudinal sides of the magazine 6. The swivel claws 13.1 are formed on the free ends of the claw arms 13.2. The claw arms 13.2 are guided by first guide pins 13.3.1, which are formed on the other ends of said claw arms and which engage in curved oblong holes 17, which are formed in the housing frame 15, and by means of second guide pins 13.3.2, which form together with a tension coupling link 14.4 a pivot joint.

A gear mechanism 14, connecting the drive motor 8 to the magazine holder 13, comprises in essence a toothed belt 14.2, two drive shafts 14.3, two worm gears 14.1, two eccentric shafts 14.5 and two tension coupling links 14.4.

The drive motor 8 drives via the toothed belt 14.2 and the two drive shafts 14.3 the self-locking worm gears 14.1, which are disposed on both sides and which have eccentric shafts 14.5 on the output side. The eccentric shafts 14.5 engage with the oblong holes 16, 17, which are formed in the middle of the tension coupling links 14.4, so that the rotary motion of the eccentric shafts 14.5 is transformed into a lifting motion. The lifting motion is transmitted to the claw arms 13.2 by means of two additional guide pins 3.3, which are formed on the ends of the tension coupling links 14.4 and which are mounted in a rotatable manner in the claw arms 13.2 and are guided in a straight oblong hole 16 formed in the housing.

The swivel claws 13.1 describe a combined swivel and lifting motion owing to the introduction of the lifting motion into the claw arms 13.2, each end of the claw arm being mounted in a curved oblong hole 17 by means of a guide pin 3.3.

In this case the swivel claws 13.1 execute only a very small and feeble rotary motion beneath the magazine 6. Then the swivel claws are pulled upwards in a straight line with a lot of force and press with the magazine 6 the pipette tips 4 against the sealing plate 2.

In contrast to the third exemplary embodiment, the contact pressure force is introduced not only in the form of a point, but also by way of the entire longitudinal side of the magazine 6, so that the pressure per unit of area and, hence, the requirements of the material of the magazine 6 are reduced.

In contrast to the first two exemplary embodiments, a different type of centering is described in this fourth exemplary embodiment. Whereas the first two exemplary embodiments provide centering cones 10, which are arranged around the sealing plate 2 and which engage with the external periphery of the magazine 6 when the magazine 6 is lifted, the fourth exemplary embodiment provides centering cones 10, which are arranged on the magazine 6 and engage with the centering openings that are provided around the sealing plate 2 in the base plate 1.

This feature has the advantage that a pipetting device according to the invention allows the magazines 6, populated with pipette tips 4, to be stacked without any additional aids in such a way that the uppermost magazine 6 can be removed from the formed stack (FIG. 9) by means of a magazine holder 13 without any additional handling devices; and this uppermost magazine can be tightened at the sealing plate 2.

This sort of centering can also be applied in a suitably adapted form to the other exemplary embodiments.

The operating principle of the fourth exemplary embodiment is shown in FIGS. 8*a-d*.

Figure 8A:
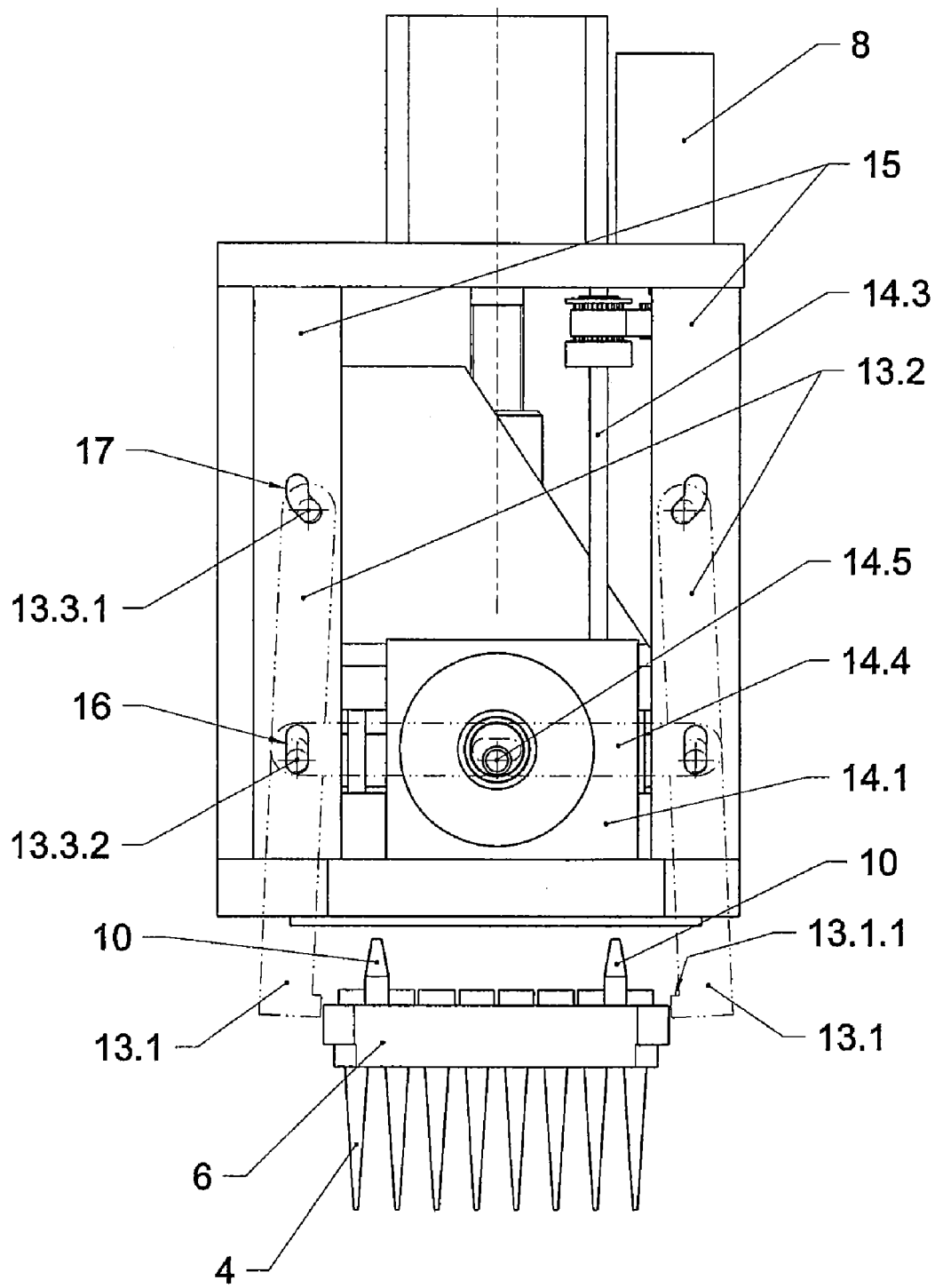
FIGS. 8a-d are in each case a cross sectional view of a pipetting device according to FIGS. 7a-b in three different states.

To begin with, the swivel claws 13.1 in FIG. 8*a* are in a position, in which they are still lowered and swung outwards.

The eccentric shafts 14.5 and, thus, also the tension coupling links 14.4 are in their bottommost position, so that the guide pins 3.3 are also in the bottommost positions in the oblong holes 16, 17.

Figure 9:
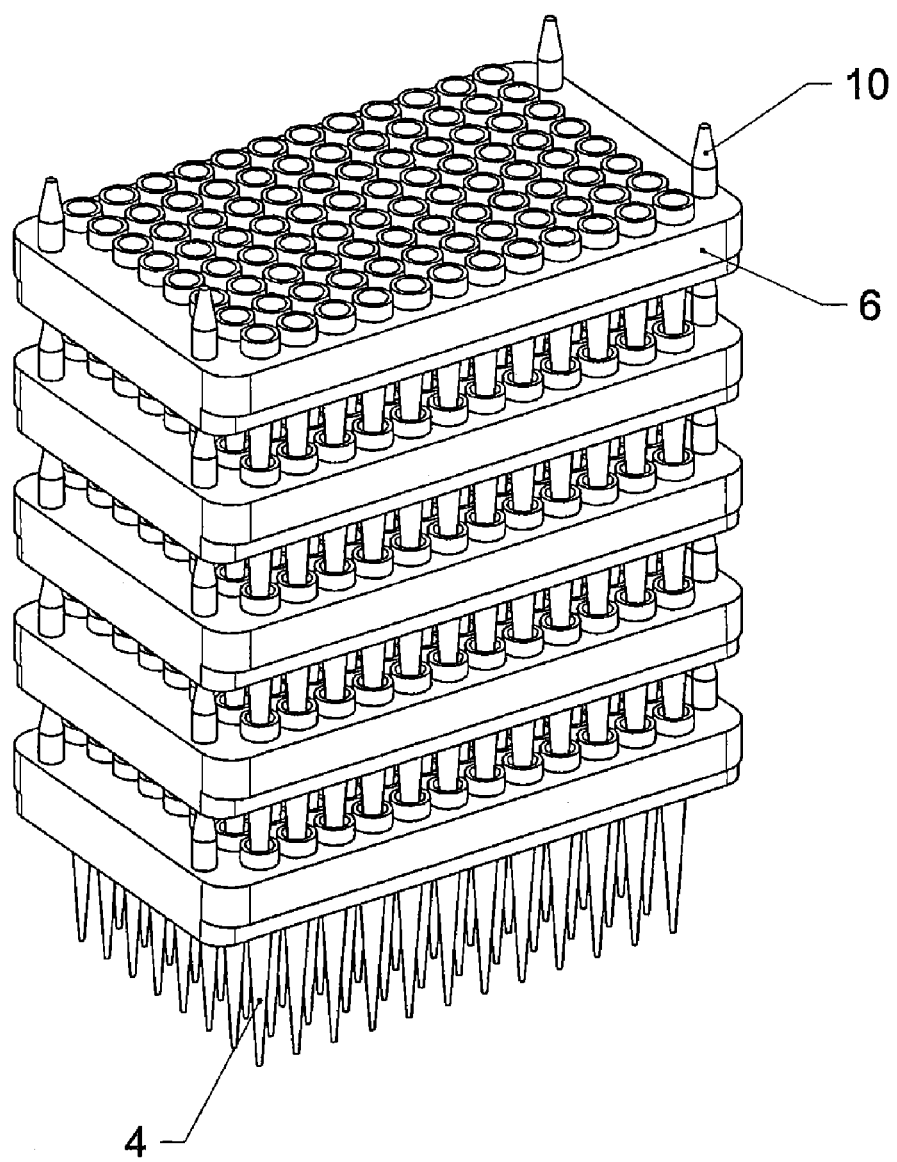
FIG. 9 shows a stack of magazines.

The magazine 6 with the pipette tips 4 is just passing the open swivel claws 13.1 and could still be lying, for example, on a stack according to FIG. 9.

Figure 8B:
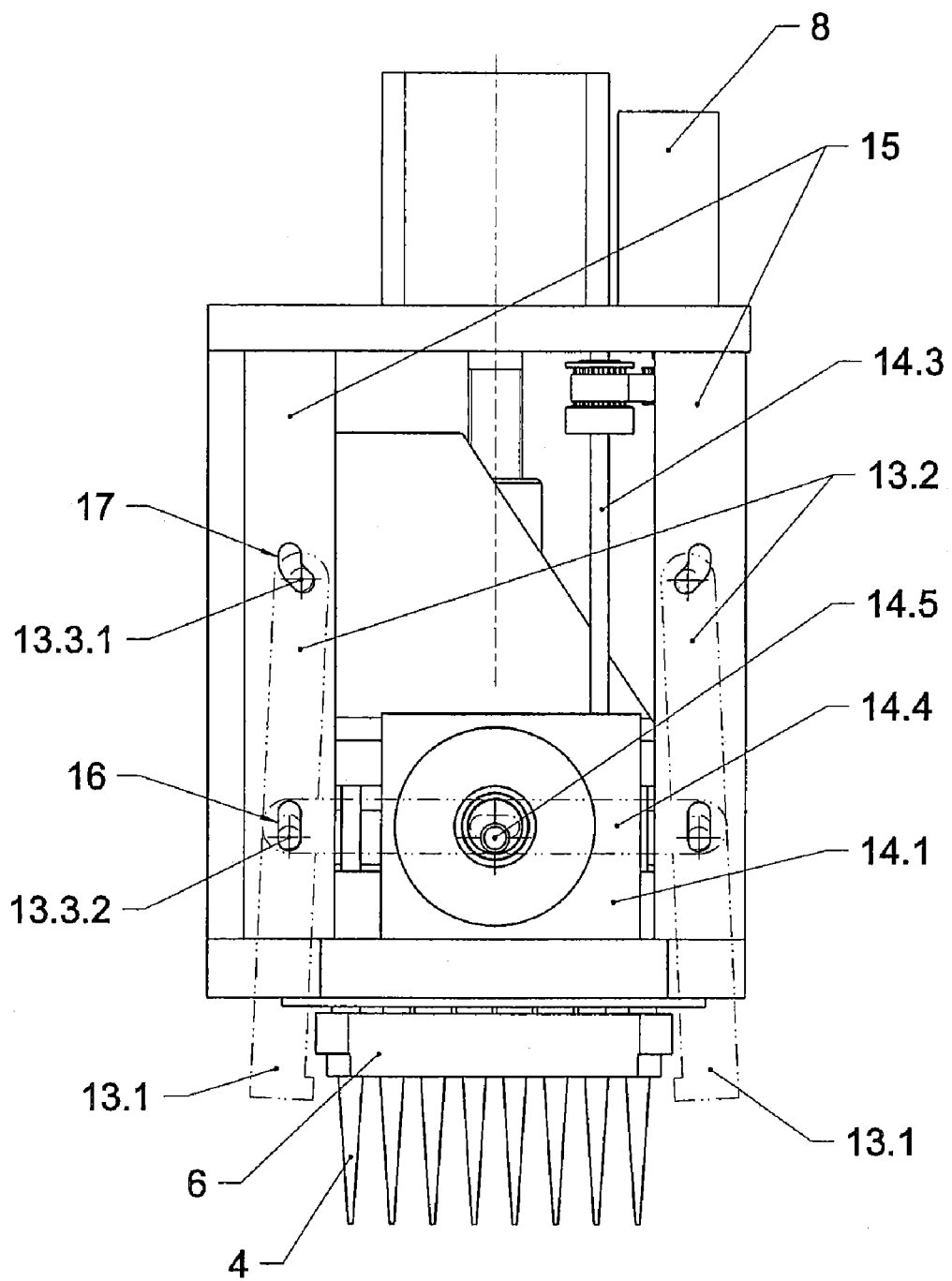

In FIG. 8*b* the magazine 6 has already been guided up to the sealing plate 2. The tip shoulders 5 rest without force against the sealing plate. During the executed lifting motion the centering cones 10, which were inserted into the centering openings, have positioned the magazine 6 relative to the pipetting system. The lifting motion was executed, as in all of the above-described exemplary embodiments, either by means of an external mechanism, which lifted the magazine 6, or by the pipetting device, which was lowered.

Figure 8C:
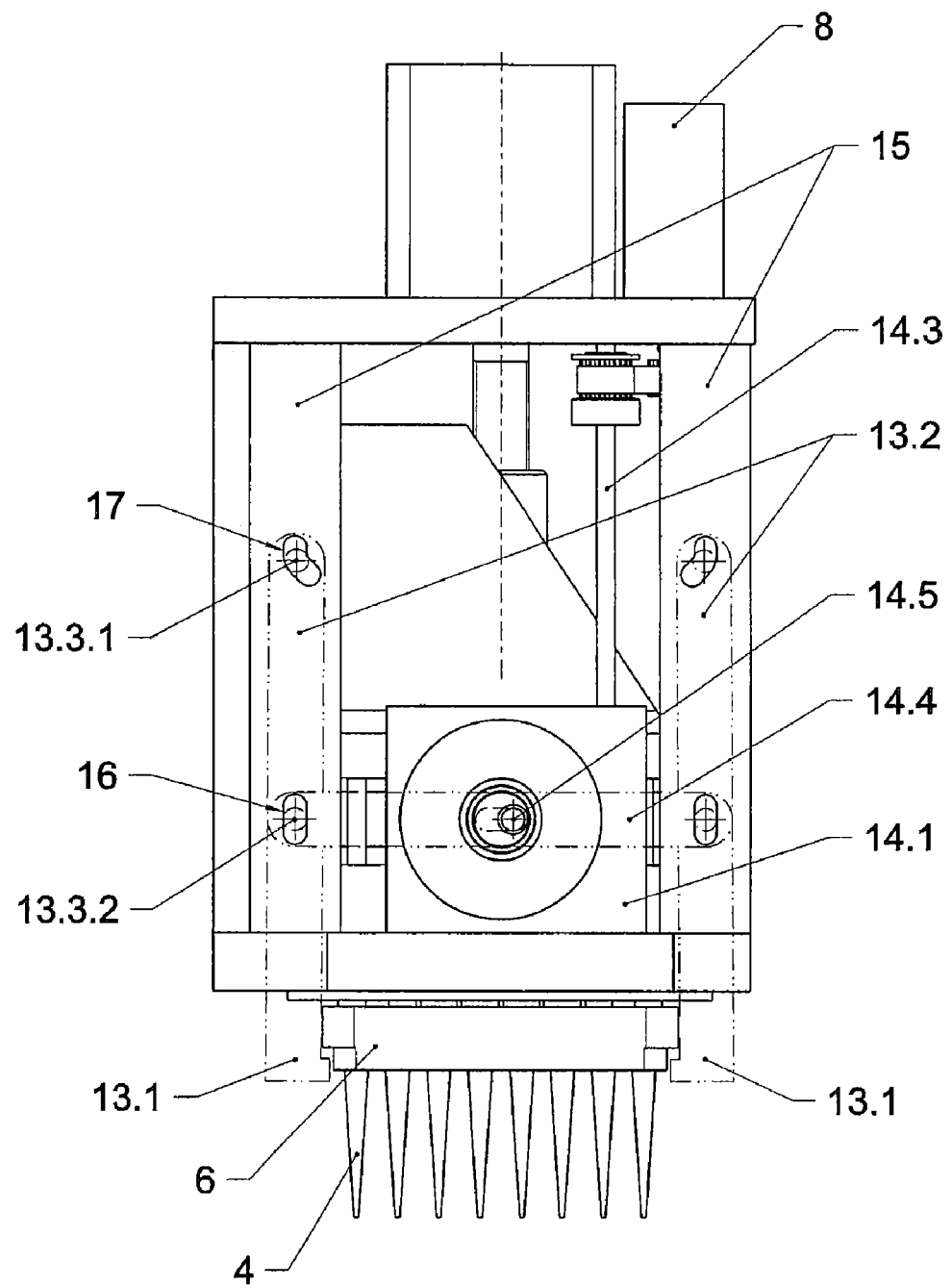

The actual tightening of the pipette tips 4 at the sealing plate 2 begins with the position shown in FIG. 8*c*. The drive motor 8 sets the worm gears 14.1 and, thus, the eccentric shafts 14.5 rotating. The tension coupling links 14.4 are pulled upwards; and the claw arms 13.2 are swiveled beneath the magazine 6 and pulled upwards.

The swiveling closes the magazine holder 13.

At the same time the guide pins 3.3 glide into the oblong holes 16, 17.

Figure 8D:
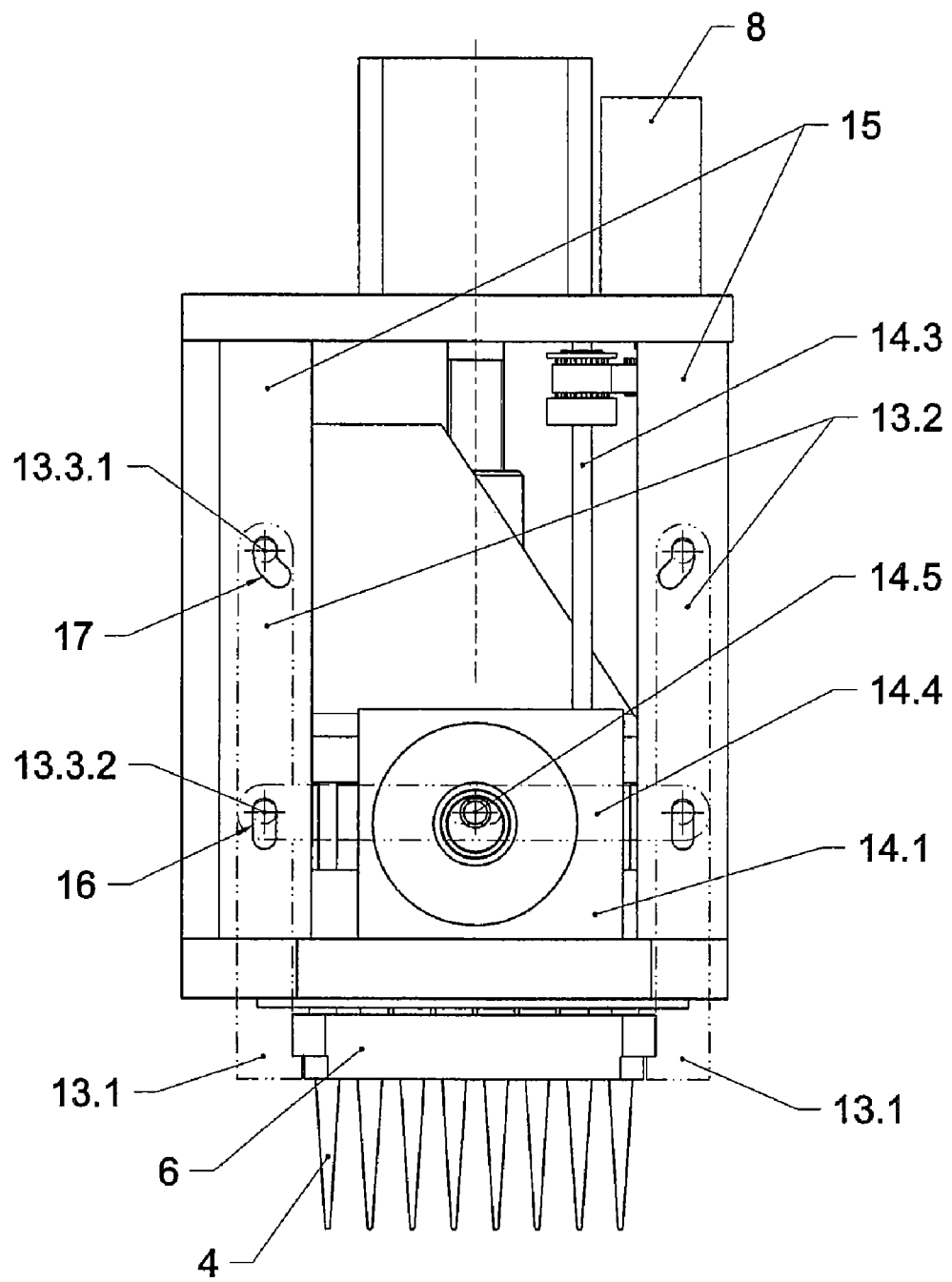

In the last segment of the lifting path, shown in FIG. 8*d*, when the eccentric shafts 14.5 generate their highest force, the guide pins 3.3 move in the perpendicular portion of the curved oblong hole 17 and press the pipette tips 4 with their tip shoulder 5 against the sealing plate 2.

The hermetic seal of all of the pipette tips 4 is reached; and the self-locking of the worm gears 14.1 maintains this state.

Since the swivel claws 13.1 are swiveled beneath the magazine 6 with practically no force, it would also be easy to solve an active drive of the swivel claws 13.1.

In this case the curved oblong holes 17 would not be needed; and an additional drive would engage with the upper guide pins 3.3.

In this case the actual tightening procedure could be reduced to a few tenths of a millimeter.

For this purpose an eccentric shaft drive with slight eccentricity could also be used. However, a piezo drive lends itself well in the optimal case, because it can make do with far fewer parts, can engage directly with the tension coupling link 14.4, and is tailored to the task in an ideal way because of its property of being able to develop high forces quickly over short paths. Although this solution needs an additional small and low performance drive, it accelerates the amount of time required to change the tips 4.

Such a solution is advantageous for applications, where the pipette tips 4 have to be frequently changed and the amount of time required for this change has a limiting effect.

A magazine 6 for a pipetting device according to the invention no longer needs a grip in order to transport the magazine by hand or by means of a gripper into the magazine holder 7, 11, 13 in conformity with the drawer principle.

LIST OF REFERENCE NUMERALS

| | List of Reference Numerals |
|---|---|
| 1 | base plate |
| 2 | sealing plate |
| 3 | pipetting channels |
| 3.1 | passage hole |
| 3.2 | piston |
| 3.3 | guide pin |
| 4 | pipette tip |
| 5 | tip shoulder |
| 6 | magazine |
| 7 | magazine holder of the first and second exemplary embodiments |
| 7.1 | swivel claw of the magazine holder of the first and second exemplary embodiments |
| 7.1.1 | support surface of the swivel claw of the magazine holder of the first and second exemplary embodiments |
| 7.2 | bearing plate |
| 7.3 | lever arm |
| 8 | drive motor |
| 9 | gear mechanism of the first and second |

-continued
List of Reference Numerals

| | |
|---|---|
| | exemplary embodiments |
| 9.1 | toothed belt |
| 9.2 | threaded spindle |
| 9.3 | drive nut |
| 9.4 | sliding coupling |
| 10 | centering cone |
| 11 | magazine holder of the third exemplary embodiment |
| 11.1 | magazine frame |
| 11.2 | stop plate |
| 11.2.1 | gliding surface |
| 11.3 | latches |
| 11.3.1 | support surface of the latches |
| 11.4 | compression spring |
| 12 | gear mechanism of the third exemplary embodiment |
| 12.1 | worm gear of the third exemplary embodiment |
| 12.2 | toothed belt of the third exemplary embodiment |
| 12.3 | drive shaft of the third exemplary embodiment |
| 12.4 | tension coupling link of the third exemplary embodiment |
| 12.5 | eccentric shaft of the third exemplary embodiment |
| 13 | magazine holder of the fourth exemplary embodiment |
| 13.1 | swivel claw of the magazine holder of the fourth exemplary embodiment |
| 13.1.1 | support surface of the swivel claw of the magazine holder of the fourth exemplary embodiment |
| 13.2 | claw arm |
| 13.3.1 | first guide pin |
| 13.3.2 | second guide pin |
| 14 | gear mechanism of the fourth exemplary embodiment |
| 14.1 | worm gear of the fourth exemplary embodiment |
| 14.2 | toothed belt of the fourth exemplary embodiment |
| 14.3 | drive shaft of the fourth exemplary embodiment |
| 12.4 | tension coupling link of the fourth exemplary embodiment |
| 14.5 | eccentric shaft of the fourth exemplary embodiment |
| 15 | housing frame |
| 16 | straight oblong hole |
| 17 | curved oblong hole |
| 18 | passage opening |

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A pipetting device, comprising
a base plate;
a plurality of pipetting channels are arranged in a defined grid in said base plate; a magazine populated with pipette tips in said grid, each of said tips having a tip shoulder; a magazine holder; a drive motor; and a gear mechanism, which connects said magazine holder and said drive motor, so that said magazine is movable vertically between an aspirating and dispensing position and a sealing position, in which the tip shoulders are non-positively connected to said pipetting channels in such a way that said tip shoulders and pipetting channels are sealed off from each other,
wherein said magazine holder is in an open state when in the aspirating and dispensing position, so as to form a passage opening larger than the magazine, so that the magazine can be inserted into the magazine holder from the bottom; and wherein the magazine holder is in a closed state when in the sealing position, in which the support surfaces, against which the magazine rests, project into the passage opening; and
wherein said gear mechanism is designed in such a way that when it is driven, not only is the magazine moved vertically, but also the magazine holder is moved into the said aspirating, dispensing and sealing positions.

2. The pipetting device, as claimed in claim 1, wherein said magazine holder comprises a closed magazine frame having a free interior that forms said passage opening and has latches, which can be axially displaced in the horizontal direction and which form the support surfaces in the closed state.

3. The pipetting device, as claimed in claim 1, wherein said magazine holder comprises two swivel claws with free ends, which define said passage opening in the open state and form the support surfaces in the closed state.

4. The pipetting device, as claimed in claim 1, wherein said magazine has centering cones and said base plate has centering openings in which the centering cones can be inserted.

5. The pipetting device, as claimed in claim 2, wherein said gear mechanism comprises a worm gear having an eccentric shaft mounted on an output side thereof and a tension coupling link mounted in a rotatable manner about one of its ends; its other end connected to said magazine frame.

6. The pipetting device, as claimed in claim 3, wherein said gear mechanism comprises a worm gear and an eccentric shaft attached thereto on an output side thereof, a tension coupling link mounted in a vertically displaceable manner on said eccentric shaft, the ends of said coupling link being connected to claw arms on which the swivel claws are formed and that are positively driven so that the swivel claws execute a combined swivel and lifting motion.

7. The pipetting device, as claimed in claim 2, wherein said base plate has stop plates with inclined sliding surfaces against which an outer end of the latches rests so that the latches are displaced during said vertical motion.

8. The pipetting device, as claimed in claim 2, wherein said two swivel claws exhibit axes of rotation that are mounted in a rotatable manner in two bearing plates, said two bearing plates connected to the base plate, and rigidly connected to one end of two lever arms, their other ends of said two lever arms being connected to said gear mechanism so that the swivel claws execute a swivel motion.

* * * * *